US007230102B2

(12) United States Patent
Giorgio et al.

(10) Patent No.: US 7,230,102 B2
(45) Date of Patent: Jun. 12, 2007

(54) DERIVATIVES OF TRIAZOLYL-IMIDAZOPYRIDINE AND OF THE TRIAZOLYLPURINES USEFUL AS LIGANDSOF THE ADENOSINE A2A RECEPTOR AND THEIR USE AS MEDICAMENTS

(75) Inventors: Tarzia Giorgio, Rome (IT); Piersanti Giovanni, Rome (IT); Giorgi Luca, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 234 days.

(21) Appl. No.: 10/484,491

(22) PCT Filed: Jul. 25, 2002

(86) PCT No.: PCT/IT02/00489

§ 371 (c)(1),
(2), (4) Date: Jan. 22, 2004

(87) PCT Pub. No.: WO03/011864

PCT Pub. Date: Feb. 13, 2003

(65) Prior Publication Data

US 2004/0204428 A1    Oct. 14, 2004

(30) Foreign Application Priority Data

Jul. 31, 2001    (IT)    .............................. RM01A0465

(51) Int. Cl.
*C07D 473/34*    (2006.01)
*C07D 471/04*    (2006.01)
*C07D 473/40*    (2006.01)
*A61K 31/52*    (2006.01)
*A61K 25/16*    (2006.01)

(52) U.S. Cl. ...................................... 544/277; 546/118
(58) Field of Classification Search ...................... None
See application file for complete search history.

(56) References Cited

U.S. PATENT DOCUMENTS

2004/0209899 A1* 10/2004 Palle et al. .............. 514/263.2

FOREIGN PATENT DOCUMENTS

| EP | 1 054 012 | 11/2000 |
| WO | 90 09178 | 8/1990 |
| WO | 96 06845 | 3/1996 |
| WO | 01 02409 | 1/2001 |

OTHER PUBLICATIONS

Hiroki Gunji, Helvetica Chimica Acta vol. 83, Issue 12, Dec. 20, 2000, pp. 3229-3245☐☐.*

Yacoubi et al.: "SCH 58261 and ZM 241385 differentially prevent the motor effects of CGS 21680 in mice: evidence for a functional "atypical" adenosine A2a receptor" European Journal of Pharmacology, vol. 401, 2000, pp. 63-77, XP002221553.
Camaioni E et al: "New Substituted 9-Alkylpurines as Adenosine Receptor Ligands" Bioorganic & Medicinal Chemistry, Elsevier Science LTD, GB, vol. 6, No. 5, 1998, pp. 523-533, XP002926121 ISSN: 0968-0896 p. 524—p. 525; tables 1,2.
Ongini E et al: "Pharmacology of Adenosine A2A Receptors" Trends in Pharmacological Sciences, Elsevier Trends Journal, Cambridge, GB, vol. 17, No. 10, (Oct. 1996), pp. 364-372, XP002123410 ISSN: 0165-6147.

* cited by examiner

*Primary Examiner*—Mark L. Berch
(74) *Attorney, Agent, or Firm*—Nixon & Vanderhye P.C.

(57) ABSTRACT

Compounds of formula (I)

wherein: X is N;
$R_1$ is $C_1$–$C_6$ linear or branched alkyl or $C_1$–$C_6$ linear or branched alkenyl; $R_2$ is hydrogen, $C_1$–$C_6$ linear or branched alkyl or $C_1$–$C_6$ linear or branched alkenyl, $C_6$–$C_{14}$ aryl or $C_6$–$C_{14}$ aryl($C_1$–$C_6$) linear or branched alkyl or $C_6$–$C_{14}$ aryl($C_1$–$C_6$) linear or branched alkenyl, with the aryl group optionally substituted by one or more substituents, either the same or different, selected from the group consisting of halogen, hydroxy, $C_1$–$C_6$ alkoxy linear or branched or $C_1$14 $C_6$ alkenyloxy linear or branched, amino, optionally mono- or disubstituted with $C_1$–$C_6$ linear or branched alkyl; $R_3$ is $NH_2$, $NHR_4$; $R_4$ is $C_1$–$C_6$ alkyl or $C_1$–$C_6$ hydroxyalkyl, $C_1$–$C_3$ alkoxyalkyl, amino($C_1$–$C_6$)alkyl, where the amino group is optionally substituted with one or two $C_1$–$C_3$ linear or branched alkyl groups, or with one or two $C_2$–$C_3$ alkenyl groups $C_6$–$C_{14}$ aryl or $C_6$–$C_{14}$ aryl ($C_1$–$C_6$)alkyl, with the aryl group optionally substituted by one or more substituents, either the same or different, selected from the group consisting by halogen, hydroxy, $C_1$–$C_6$ alkoxy linear or branched or $C_1$–$C_6$ alkenyloxy linear or branched, amino, mono- or di-substituted with $C_1$–$C_6$ alkyl linear or branched or $C_1$–$C_6$ alkenyl linear or branched; and their pharmaceutically acceptable salts. These compounds are antagonists of the adenosine $A_{2a}$ receptor and useful as medicaments, in particular for the treatment of Parkinson's disease.

6 Claims, 5 Drawing Sheets

FIGURE 1

Cataleptogenic potential of ST 1535 and ST 1537 compared with that of CGS 21680 ( $A_{2a}$ selective agonist) and of ZM 241385 ( $A_{2a}$ selective antagonist).

FIGURE 2

Effect of ST 1535 (5 mg/Kg and 10mg/Kg; p.o.) on CGS 21680--induced catalepsy. Each column represents mean score catalepsy ± s.e. of 10 animals per group.

FIGURE 3

Effect of ST 1535 (2.5 mg/Kg - 20 mg/Kg, p.o.) on Haloperidol induced catalepsy, in mice. Each column represents the mean catalepsy score ± s.e. of 10 animals per group.

FIGURE 4

Combination effects of ST 1535 (1.25mg/kg and 2.5 mg/Kg, p.o.) with sub threshold dose of L-DOPA plus benserazide (12.5 mg/kg and 6.25 mg/kg, i.p., respectively) on Haloperidol -induced catalepsy in mice

FIGURE 5

Effect of ST 1535 (1.25mg/Kg, 2.5 mg/Kg; 5mg/Kg, 10 mg/Kg); p.o.) in mouse forced swim test. Mice were injected with vehicle or ST 1535 or Imipramine 60 minutes before the test. The duration of immobility was recorded during 4 minutes of the testing period. Data represented are mean ± s.e. of 10 mice per group. ANOVA and Tukey's test **= $p < 0.01$ vs. controls.

DERIVATIVES OF TRIAZOLYL-IMIDAZOPYRIDINE AND OF THE TRIAZOLYLPURINES USEFUL AS LIGANDS OF THE ADENOSINE A2A RECEPTOR AND THEIR USE AS MEDICAMENTS

This application is the US national phase of international application PCT/IT02/00489, filed in English on 25 Jul. 2002, which designated the US. PCT/IT02/00489claims priority to IT Application No. RM01A000465 filed 31 Jul. 2001. The entire contents of these applications are incorporated herein by reference.

The present invention relates to derivatives of triazolyl-imidazopyridine and of the triazolylpurines, useful as ligands of the adenosine $A_{2a}$ receptor, to a process for their preparation, to their uses as medicaments, in particular, for the treatment of pathologies which benefit from the inhibition of this receptor, and to the pharmaceutical compositions comprising them.

BACKGROUND OF THE INVENTION

Current therapy for Parkinson's disease is limited to the alleviation of the symptoms, but no agent has yet been identified capable of counteracting the establishment and the progress of the degeneration of the dopaminergic neurons of the substantia nigra linked with deficient dopamine levels of the basal ganglia in turn responsible for the appearance of the complex symptomatology of this pathology. This is characterised by rigidity, tremors, bradykinesia, akinesia, posture changes; manifestations that represent a serious threat to the health of the individual with Parkinson's disease.

Among the therapeutic strategies currently used to improve the quality of life of these subjects, are therapeutic approaches which aim to replenish the missing neurotransmitter. One example is represented by the use of L-DOPA, in combination with carbidopa or benserazide (inhibitors of the peripheral amino acid decarboxylases enzymes). This therapy is one of the most effective and currently used against the appearance of changes in motor function which are manifested when the physiology of the dopaminergic system is severely compromised.

However, in the long run, this therapeutic approach is subject to a lowering of efficacy. Indeed, patients subjected to chronic treatment with L-DOPA frequently display an emphasising of said manifestations, in addition to the appearance of other side effects, due to the inherently neurotoxic properties possessed by L-DOPA.

Alternatively, the use of dopaminergic receptor agonists has been introduced, however they do not display the same efficacy as L-DOPA; or of monoamine oxidase inhibitors and of the muscarinic acetyl choline receptor antagonists. The use of the latter brings about the appearance of serious side effects and cognitive impairment, as a consequence of the receptor interactions these products establish, both at the systemic level and at the central nervous system level.

In recent years, with the discovery of the role of adenosine as a neurotransmitter, its receptors and their functional characterisation, the hypothesis of using antagonists of the adenosine $A_{2a}$ receptor as therapeutic agents for the treatment of the motor disorders associated with Parkinson's disease has gained credit. (P. J. Richardson, H. Kase and P. G. Jenner *Trends Pharm. Sci* 1997, 18:338–345).

Recent experimental evidence has allowed the understanding of the distribution, the function and the physiology of this receptor at the level of the central nervous system, permitting the conclusion that blocking the $A_{2a}$ receptor can modulate cholinergic, gabaergic and glutamatergic neurotransmission, in order to establish at the level of the basal ganglia output neurons, a neurochemical order which can adequately compensate acute or chronic Dopamine deficiency in the nigrostriatal system.

Furthermore, it has been observed that the $A_{2a}$ receptor is functionally associated with that for Dopamine $D_2$ and that the stimulation of the former can reduce the binding capacity of the latter for Dopamine. Thus it follows, that the blocking of the $A_{2a}$ adenosine receptor increases the interactive capacity of $D_2$ receptors towards Dopamine, favouring binding even in the presence of low levels of this neurotransmitter in the synaptic space. (Ferre S., e al. (1991) *Proc. Nat. Acc. Sci. U.S.A.* 88, 7237–7241). For these reasons, selective antagonists of the $A_{2a}$ receptor have been proposed as agents for the treatment of motor disorders, with particular regard to Parkinson's disease.

In addition, it has been demonstrated that these agents offer an effect that is synergic to the treatment with L-DOPA or with dopamine agonists, and can be used in conjunction with the Dopamine-substitutive therapies. In this case, the use of receptor $A_{2a}$ selective antagonists represents a further therapeutic advantage since, the dosages normally required for L-DOPA therapeutic treatment could be reduced in quantity, or frequency of administration, thereby conserving the therapeutic efficacy.

The present invention relates to compounds with affinity for the adenosine $A_{2a}$ receptor, active as antagonists, useful in the preparation of medicaments for the treatment of motor disorders in individuals, which are associated with functional alterations in the basal ganglia, forming part of the symptomatology of diseases such as Parkinson's disease, Alzheimer's disease, Huntington's disease and Wilson's disease; brought about by drugs (parkinsonism of classic neuroleptics) trauma, toxic agents (NOTP, manganese, carbon monoxide).

The present invention can also be used in the treatment of Parkinson's disease with "on-off" phenomena and Parkinson's disease with preponderant dyskinesia.

In addition, having been demonstrated that, following ischaemic damage to the central nervous system, adenosine $A_{2a}$ receptor antagonists can inhibit the toxic effects induced by the excitatory amino acids released in abundance after such phenomena, cerebral ischaemia and the mechanisms associated with neurodegenerative processes represent other "targets" towards which $A_{2a}$ receptor antagonists can display their therapeutic actions.

Selective antagonists of the adenosine $A_{2a}$ receptor are described in CA 1.242.368, Boehringer Ingelheim, in the form of imidazo-triazole-pyrimidine derivatives, in which their activity towards the $A_1$ receptor prevails towards the $A_2$ receptor; in WO 01/02409, Vernalis Res Ltd, derivatives of thieno- and furopyrimidine are described as compounds useful in the treatment of motor disorders, for example Parkinson; WO 00/24742, Fusijawa Pharm Co Ltd, describes derivatives of pyrazolopyridine with dual antagonistic action against the $A_1$ and $A_2$ receptors; WO 00/17201 and WO 98/42711, Kyowa Hakko KKK, describe derivatives of 1,2,4-triazolo-(1,5-c)pyrimidine; WO 00/13682, WO 00/13681 and WO 99/26627, Cerebrus Pharm Ltd, describe derivatives of 4-quinolinemethanol; WO 99/62518, Cadus Pharm Corp, describe 7-deazapurine N-6 substitu tions with activity profiles as $A_1$, $A_2$, $A_{2a}$, $A_{2b}$, $A_3$ receptor antagonists; WO 99/43678, Kyowa Hakko KKK, describe derivatives of 1,2,4-triazolo-(1,5-a)-pyrimidine; WO 95/01356 and WO 98/52568, Schering Plough SpA, describe 1,2,4-triazolo-(1,5-c)-pyrimidine.

Amongst the $A_{2a}$ receptor antagonists in advanced testing phase, we can mention compounds KW-6002 and KW-1783, described in EP 0 628 311, which can be characterised as xanthine derivatives. These products possess a (3,4-dimethoxyphenyl)ethylenic group in position 8, and are subject to loss of activity through photoisomerisation of the ethylenic bond (*Annals New York Academy of Sciences*—Ongini E.; Adami M; Ferri C; and Bertorelli R.; *Trends in Pharm. Sci.* 1996 Vol. 17 364–72). The compound KW 6002 is currently undergoing clinical trials (phase II as an antidepressant and phase III as an antiparkinson agent; *Pharmaprojects* Acc. No. 23891). Another selective antagonist of the $A_2$a receptor is the product SCH 63390 (*Pharmaproject* Acc. No29842), in pre-clinical trials. ZM 241385 from Astra Zeneca (EP 0 459 702) is a potent selective antagonist; for this reason, utilised for pharmacological investigations (Ji X. D., Jacobson K. A., *Drug Des. Discov.* 1999, 16:217–226; *Pharmaproject* Acc. No 22730). Despite its high selectivity and affinity, in vivo the product has shown very low bioavailability (El Yacoubi M.; et al *Eur. J. Pharm.* 401 (2000) 63–77).

SUMMARY OF THE INVENTION

It has been found that compounds with the formula (I)

where: X is N, CH, C—$R_2$;

$R_1$ is $C_1$–$C_6$ linear or branched, saturated or unsaturated alkyl;

$R_2$ is hydrogen, $C_1$–$C_6$ linear or branched saturated or unsaturated alkyl, $C_6$–$C_{14}$ aryl or $C_6$–$C_{14}$ aryl($C_1$–$C_6$) linear or branched, saturated or unsaturated alkyl with the aryl group optionally substituted by one or more substituents, the same or different, selected from the group consisting of halogen, hydroxy, $C_1$–$C_6$ linear or branched, saturated or unsaturated alkoxy, amino, mono- or di-$C_1$–$C_6$ linear or branched alkyl;

$R_3$ is NH2, NHR$_4$ $R_4$ is $C_1$–$C_6$ alkyl or $C_1$–$C_6$ hydroxyalkyl, $C_1$–$C_3$ alkoxyalkyl, amino($C_1$–$C_6$)alkyl, where the amino group is optionally substituted by one or two $C_1$–$C_3$ alkyl groups, said alkyl groups are either linear or branched saturated or unsaturated, $C_6$–$C_{14}$ aryl or $C_6$–$C_{14}$ aryl($C_1$–$C_6$)alkyl, with the aryl group optionally modified by one or more substituents, the same or different, selected from the group constituted by halogen, hydroxy, $C_1$–$C_6$ alkoxy linear or branched saturated or unsaturated, amino, mono- or di-substituted by $C_1$–$C_6$ alkyl linear or branched saturated or unsaturated and pharmaceutically acceptable salts thereof, possess affinity for the $A_{2a}$ receptor.

Therefore, an object of the present invention are formula (I) compounds defined above and the pharmaceutically acceptable salts thereof Another object of the present invention are the processes for the preparation of formula (I) compounds defined above, their use as medicaments, in particular for the preparation of medicaments with inhibitory activity, also selectively, of the $A_{2a}$ adenosine receptor, such medicaments being useful for the treatment of pathologies responsive to the inhibition of the adenosine $A_{2a}$ receptor, such as the treatment of motor disorders, Alzheimer's disease, Huntington's disease, Wilson's disease and Parkinson's disease. The compounds according to the present invention are also useful for the preparation of medicaments for the treatment of cerebral ischaemia and/or the mechanisms associated with neurodegenerative processes.

Further objects of the present invention are pharmaceutical compositions which contain at least one formula (I) compound as active ingredient.

BRIEF DESCRIPTION OF DRAWINGS

This and other objects of the present invention will be illustrated in greater detail also by figures and examples, where.

The duration of immobility was recorded during 4 minutes of the testing period. Data represented are mean±s.e. of 10 mice per group. ANOVA and Tukey's test \*\*=p<0.01 vs. controls.

DETAILED DESCRIPTION OF THE INVENTION

In the formula (I) compounds, examples of $C_1$–$C_6$ saturated or unsaturated alkyls are methyl, ethyl, propyl, isopropyl, butyl, sec-butyl, ter-butyl, pentyl, hexyl, ethylene, propylene, butylene. The alkenyls and the alkinyls may contain up to the maximum possible degree of unsaturation, and the alkyls, alkenyls and alkinyls may be represented by all the theoretically possible isomers. In the formula (I) compounds, examples of $C_6$–$C_{14}$ aryl or $C_6$–$C_{14}$ aryl($C_1$–$C_6$) alkyl, with the optionally substituted aryl group are phenyl, naphthyl and anthryl, at various bond positions (for example 1- or 2-naphthyl), benzyl, phenylethyl, phenylpropyl, phenylbutyl, phenylpentyl, phenylhexyl, arylalkyl analogues with naphthyl and anthryl, 2-, 3- or 4-phenyl groups substituted by the above mentioned groups, for example 2-, 3- or 4-hydroxyphenyl, 2-, 3- or 4-alkoxyphenyl, where the alkyl residue is as described above, 2-, 3- or 4-halophenyl, where the halogen is fluoro, chloro, bromo, iodo, 2-, 3- or 4-aminophenyl, where the amino group can be mono or di substituted with an alkyl group as described above. The person skilled in the art will easily be able to characterise all the possible compounds predicted for formula (I) defined above, making the appropriate substitutions with the definitions given for the various groups.

Pharmaceutically acceptable salts of formula (I) compounds are all these with organic or inorganic acids capable of salifying the basic centres present, and which do not possess any toxic or otherwise undesired effects.

Amongst the formula (I) compounds, a first preferred group comprises those wherein X is nitrogen and $R_2$ is a butyl group in position 2.

A second preferred group is comprised of those wherein X is nitrogen and $R_2$ is a phenethyl group in position 2.

A third preferred group is comprised of those wherein X is nitrogen and $R_2$ is a pentyl group in position 2.

A fourth preferred group is comprised of those wherein X is carbon and $R_2$ is hydrogen in position 6 or 7.

The following compounds are particularly preferred:
6-amino-2,9-dimethyl-8-(triazol-2-yl)-9(H)-purine (ST 1491);
2-butyl-9-methyl-8-(2H-1,2,3-triazol-2-yl)-9H-purine-6-ylamine
(ST 1535);
9-methyl-2-(2-phenylethyl)-8-(2H-1,2,3-triazol-2-yl)-9H-purine-6-ylamine (ST 1537);
9-methyl-2-pentyl-8-(2H-1,2,3-triazol-2-yl)-9H-purine-6-ylamine (ST 2097).

As a particular case of the present invention, the compound 6-amino-9-methyl-8-(triazol-2-yl)-9(H)-purine (ST 1490) revealed affinity toward the $A_1$ adenosine receptor, therefore is useful for the preparation of a medicament for the treatment of cognitive deficits, Alzheimer's disease, cerebral ischemia, acute and chronic renal failure, renal failure induced by radiografic contrast media or by cisplatin.

Formula (I) compounds can be prepared following the synthetic approach described in the following diagram.

Compound a), obtainable through methods known in the literature, is subjected to be bromo-substituted at position 2, then the bromo is substituted by the triazol-2-yl group.

The following diagrams 1A, 1Abis and 2A show, by way of example only, the processes for the preparation of the compounds briefly denominated ST 1491, ST 1536, ST 1535, ST 1537, ST 2097 and ST 1680.

SCHEME 1A

The compounds indicated by the numbers (2) to (7) (diagrams 1A and 1Abis) are obtained by synthetic procedures known in the literature, compound (1) is commercially available; compounds (8), (9) and (10), are described in *Heterocycles* 1999, 721–726; *J.Med.Chem.*32, 11, 1989, 2474–2485; *J. Heter. Chem.* 23, 3, 1986, 669–672; *J. Chem. Soc.* 1955, 2755–2758; *J. Med. Chem.* 39, 2, 1996, 487–493; *J. Heter. Chem.* 27, 3, 1990, 563–566; (11) and (12) are described in EP 0 082 369 but the present invention provides a new preparation. The molecules from (13) to (14) are new, therefore they are specifically claimed as intermediates of the process described in the present invention. Persons skilled in the art, resorting to their general knowledge and to the literature, are able to prepare the other formula (I) compounds, different from these exemplified in the preceding diagrams.

The following examples further illustrate the invention.

EXAMPLE 1

Scheme 1A 2-chloro-6-dibenzylamino-9(H) Purine (2)

To a solution of 1 g of 2,6-dichloropurine (1) (97%, 5.13 mmol), in 30 ml of absolute ethanol were added di-isopropylethylamine (1 ml, 5.13 mmol) and distilled dibenzylamine (1.1 ml, 5.13 mmol). The reaction mixture was left to reflux for 20 hours (after 1 hour a white precipitate is formed). The solvent was then removed at low pressure and the residue taken up in water.

Following cooling and filtration the solid residue (2), was dried under vacuum.

Yield: 95% $R_f$=0.25 (cyclohexane/ethyl acetate) 7:3 M.p.: 250–252° C. $^1$H-NMR (200 MHz, CDCl$_3$): δ 7.89 (s, 1H), 7.32 (s, 10H), 5.55 (bs, 2H), 5.49 (bs, 2H). MS (m/z): 91; 258–260 (BP, M-benzyl), 349–351 (<5%, M).

2-chloro-6-dibenzylamino-9-methyl-purine (3)

To a solution of (2) in hot DMF was added 828 mg of K$_2$CO$_3$ (6 mmol). The solution was then cooled and treated with 0.46 ml of CH$_3$I (7.2 mmol) with agitation for about 12 hours. The DMF was evaporated, the product taken up in water and filtered, and the residue obtained crystallised in ethanol giving 1.45 g of product (3)

Yield: 78%. $R_f$=0.38 (cyclohexane/ethyl acetate) 7:3. M.p.: 144–146° C. $^1$H-NMR (200 MHz, CDCl$_3$): δ 7.67 (s, 1H, H8-purine); 7.31 (s, 10H, aromatic); 5.5 (br, 2H, CH$_2$-benzylate); 4.93 (br, 2H, CH$_2$-benzylate); 3.81 (s, 3H, CH$_3$). MS (m/z): 91 (BP, benzyl); 272–274 (65%–20%, M-benzyl), 363–365 (<5%, M).

2-alkyl-6-dibenzylamino-9-methyl-9(H)-purine (4), (4c), (4e), (5)

(General procedure) In a nitrogen-filled flask were placed 700 mg of 2-chloro-6-dibenzylamino-9-methyl-9(H)-purine (3) (1.93 mmol), 4 ml of NMP (N-methylpyrrolidone), 3.8 mmol of alkyl tributyl tin and 140 mg of Pd(PPh$_3$)$_4$. These were stirred at 120° C., for 8 hours for compounds 4, 4c and 4e and two hours for compound 5. These were cooled and diluted with water (50 ml) and methylene chloride (50 ml) and the aqueous phase finally extracted with methylene chloride (4×50 ml). The combined organic phases were washed in salt water, dried over anhydrous sodium sulphate and the solvent evaporated thus obtaining a dark liquid. The products were purified on a silica-gel column, (eluent: EtOAc/Cyclohexane 1/1) giving (4), (4c), (4e) and (5) in the form of solids or yellow oils.

(4): Yield: 63%. M.p.: 143° C. MS (m/z): 278 (100%, M-benzyl); 91 (55%, benzyl).

(4c): Yield: 90%. M.p.: non-determinable—rubber-like substance. MS (m/z): 294 (100%, M-benzyl); 91 (65%, benzyl). $^1$H-NMR: 200 MHz, CDCl$_3$; δ 7.65 (1H, s, purine); 7.30 (10H, m, aromatics); 5.27 (4H, br, —CH$_2$—benzylate); 3.82 (3H, s, N—CH$_3$); 2.88 (2H, t, —CH$_2$—CH$_2$—CH$_2$—CH$_3$); 1.80 (2H, m, —CH$_2$—CH$_2$—CH$_2$—CH$_3$); 1.37 (2H, t, —CH$_2$—CH$_2$—CH$_2$—CH$_3$); 0.91 (3H, t, —CH$_2$—CH$_2$—CH$_2$—CH$_3$).

(4e) Yield: 65%.

6-dibenzylamino-9-methyl-2-pentyl-9(H)-purine

M.p.: non-determinable, rubber-like substance. MS: m/z=399, 308, 220 $^1$H-NMR (200 MHz, CDCl3) δ (ppm): 7.71 (s, 1H), 7.30 (m, 10H), 5.30 (bs, 4H), 3.80 (s, 3H), 3.38 (t, 2H), 2.38 (m, 2H), 2.02 (m, 2H), 1.30 (m, 2H), 0.88 (m, 3H)

(5): Yield: 84%. M.p.: non-determinable—rubber like substance. MS (m/z): 340 (100%, M-benzyl); 91 (70%, benzyl).

6-dibenzylamino-2,9-dimethyl-9(H)-purine (4a)

In a refrigerated, three-necked, round-bottomed flask, under an inert atmosphere (nitrogen), were placed 1.07 g of (3) (2.94 mmol) dissolved in 30 ml of anhydrous THF, 6 ml of trimethylaluminium 2M in toluene (12 mmol), 27 mg of PdCl$_2$ (0.15 mmol) and 79 mg of PPh$_3$ (0.3 mmol). These were reacted by refluxing for 48 hours. Terminating the reaction, the mixture was poured into a beaker, chilled in an ice bath and the excess trialkylaluminium destroyed by small additions of water and alcohol. The aluminium hydroxide precipitate was filtered through paper, and the mixture extracted with dichloromethane. Following evaporation of the organic phase at reduced pressure the residue was purified by flash chromatography (SiO$_2$, cyclohexane/EtOAc 1:1). 900 mg of (4a) (2.62 mmol) in crystalline form were obtained.

Yield 89%. M.p.: 117–118° C. MS (m/z): 91 (80%, benzyl), 252 (BP M-benzyl), 343 (<5%, M). $^1$H-NMR: 200 MHz, CDCl$_3$ δ 7.65 (s, 1H, H8-purine); 7.30 (s, 10H, aromatics); 5.30 (br, 4H, CH$_2$-benzylate); 3.81 (s, 3H, N—CH$_3$); 2.62 (s, 3H, C—CH$_3$).

2-isoproyl-6-dibenzylamino-9-methyl-9(H)-purine (4b) and 2-(2-phenylethyl)-6-dibenzylamino-9-methyl-9(H)-purine (4d)

100 mg of (4) or (5) were placed in an autoclave with 5 ml of ethanol, heated until completely dissolved and then 50 mg of palladium on graphite support added. This was left stirring overnight under 4 atmospheres of hydrogen. The catalyst was filtered through celite and the solvent evaporated under reduced pressure, giving (4b) or (4d) as white solids.

(4b): Quantitative yield. M.p.: 82° C. MS m/z: 280 (100%, M-benzyl); 91 (50%, benzyl).

(4d): Quantitative yield. M.p.: 144° C. MS m/z: 342 (100%, M-benzyl); 91 (100%, benzyl).

Scheme 1A bis (5a,b,c,d,e)

General Procedure

In a reaction flask were solubilised 1.6 mmol of (4a), (4b), (4c), (4d) and (4e) in a mixture of 7 ml of MeOH, 7 ml of THF and 7 ml of acetate buffer pH=4 (obtained by dissolving 4 g of sodium acetate in 100 ml of water and bringing to pH 4 with glacial acetic acid). 0.7 ml of bromine (13.6 mmol) were added very slowly dropwise and the mixture left at room temperature under stirring until the starting products had disappeared (about 12 hours). Excess bromine was decoloured with sodium metabisulphite and the reaction alkalinised to pH=8 with a saturated solution of Na$_2$CO$_3$. After extraction with dichloromethane and evaporation of the solvent at reduced pressure, 1.2 g of yellow oil were obtained for (5a), (5b), (5c), (5d) (5e), later purified on preparative chromatographic column.

(5a): Quantitative yield. MS m/z: 91 (100%, benzyl); 330–332 (doublet, 70%, M-benzyl).

(5b): Quantitative yield. MS (m/z): 91 (100%, benzyl); 358–360 (doublet, 70%, M-benzyl).

(5c): Quantitative yield. MS m/z: 91 (100%, benzyl); 372–374 (doublet, 70%, M-benzyl).

(5d): Quantitative yield. MS (m/z): 91 (100%, benzyl); 420–422 (doublet, 45%, M-benzyl).

(5e)

9-bromo-6-dibenzylamino-9-methyl-2-pentyl-9(H)-purine

M.p.: 97° C. MS: m/z=479–477, 388–386 $^1$H-NMR (200 MHz, CDCl$_3$) δ (ppm): 7.28 (m, 10H), 5.16 (bs, 4H), 3.75 (s, 3H), 2.79 (t, 2H), 1.79 (m, 2H), 1.29 (m, 4H), 0.86 (m, 3H)

2-Alkyl-6-dibenzylamino-9-methyl-8-(triazol-2-yl)-9 (H)-purine (6a,b,c,d,e)

In a reaction flask, under an inert atmosphere, were placed 2 ml of anhydrous DMF, 92 mg of NaH (80% in paraffin, 2.5 mmol) and slowly, 0.18 ml of 1,2,3-triazole (2.5 mmol) were added and left under stirring for about 1 hour. A solution of crude (5a),(5b), (5c), (5d) or (5e) (1.7 mmol) in 5 ml of anhydrous DMF was added dropwise, slowly and left under stirring at 100° C. for 12 hours. The DMF was evaporated and the residue purified by flash chromatography (SiO$_2$, cyclohexane/EtOAc 7:3) giving (6a), (6b), (6c), (6d) or (6e) as white solids.

(6a): Yield: 20%. M.p.: 161–163° C. MS (m/z):91 (90%, benzyl), 319 (BP, M-benzyl); 410 (<5%, M). $^1$H-NMR: 200 MHz, CDCl3: δ 7.94 (s, 2H, H-triazole); 7.29 (s, 10H aromatics); 5.45 (br, 2H, CH$_2$-benzylate); 5.04 (br, 2H, CH$_2$-benzylate); 3.96 (s, 3H, N—CH$_3$); 2.62 (s, 3H, C—CH$_3$).

(6b): Yield 20%. M.p.: 140° C. MS (m/z): 347 (100%, M-benzyl); 91 (75%, benzyl).

(6c): Yield 20%. M.p.: 114° C. MS (m/z): 361(100%, M-benzyl); 91(70%, benzyl). $^1$H-NMR: 200 MHz, CDCl$_3$; δ 7.94 (2H, s, triazole); 7.30 (10H, m, aromatics); 5.49–5.21 (4H, d, br, —CH$_2$— benzylate); 4.12 (3H, s, N—CH$_3$); 2.84 (2H, t, —CH$_2$—CH$_2$—CH$_2$—CH$_3$); 1.80 (2H, m, —CH$_2$—CH$_2$—CH$_2$—CH$_3$); 1.37 (2H, m, —CH$_2$—CH$_2$—CH$_2$—CH$_3$); 0.92 (3H, t, —CH$_2$—CH$_2$—CH$_2$—CH$_3$).

(6d): Yield 20%. M.p.: 173° C. MS (m/z): 409 (65%, M-benzyl), 91 (100%, benzyl).

(6e)

6-dibenzylamino-9-methyl-2-pentyl-8-(triazol-2-yl)-9(H)-purine

M.p.: 139° C. MS: m/z=466, 375, 348 $^1$H-NMR (200 MHz, CDCl$_3$) δ (ppm): 7.94 (s, 2H), 7.29 (m, 10H), 5.47 (bs, 2H), 5.04 (br, 2H), 3.96 (s, 3H), 2.84 (t, 2H), 1.82 (m, 2H), 1.33 (m, 4H), 0.88 (m, 3H)

2-Alkyl-6-amino-9-methyl-8-(triazol-2-yl)-9(H)-purine (7a,b,c,d,e)

In a refrigerated reaction flask under nitrogen, were dissolved 0.33 mmol of (6a), (6b), (6c), (6d) or (6e) in 3 ml of anhydrous dichloromethane. 0,37 ml of CF$_3$SO$_3$H (3.3 mmol) were added slowly, dropwise, and the mixture left refluxing for six hours. The mixture was then loaded onto an activated alumina chromatographic column, firstly eluted with 50 ml of dichloromethane to eliminate the strongly coloured aromatic derivatives, and then with CH$_2$Cl$_2$/ethanol 1:1 (40 ml), followed by ethanol (40 ml) and finally with saturated aqueous ammonia in ethanol (5%, 40 ml). The moieties containing the desired product were combined and evaporated, giving a yellow solid which was purified by flash chromatography (SiO$_2$, AcOEt/EtOH 95:5), giving the pure products (7a,b,c,d,e) as white solids. Crystallisation in ethanol gave highly pure product in the form of small, very white crystals.

(7c) (ST 1535)

Yield: 55%. M.p.: 182° C. MS (m/z): 230 (100%, M-42); 243 (20%, M-29); 257 (10%, M-15); 272 (<10%, M). $^1$H-NMR: 200 MHz, CDCl$_3$; δ 8.00 (2H, s, triazole); 5.74 (2H, br, —NH$_2$); 4.07 (3H, s, N—CH$_3$); 2.85 (2H, t, —CH$_2$—CH$_2$—CH$_2$—CH$_3$); 1.79 (covered by water, m, —CH$_2$—CH$_2$—CH$_2$—CH$_3$); 1.43 (2H, m, —CH$_2$—CH$_2$—CH$_2$—CH$_3$); 0.97 (3H, t, —CH$_2$—CH$_2$—CH$_2$—CH$_3$).

(7b) (ST 1536)

Yield: 55%. M.p.: 177° C. $^1$H-NMR: (200 MHz, CDCl$_3$) δ 8.00 (2H, s, triazole); 5.70 (2H, br, —NH$_2$); 4.07 (3H, s, N—CH$_3$); 3.10 (1H, sextuplet (J=6.82 Hz), CH$_3$—CH—CH$_3$); 1.36 (6H, d (J=6.82 Hz), CH$_3$—CH$_2$—CH$_3$). MS: m/z: 230 (100%, M-28); 243 (95%, M-15); 216 (50%, M-44); 258(50%, M).

(7d) (ST 1537)

Yield: 55%. M.p.: 164° C. $^1$H-NMR (200 MHz, CDCl$_3$): δ 8.00 (2H, s, triazole); 7.3–7.18 (5H, m, arom.); 4.07 (2H, s, CH$_2$); 3.17 (2H, s, CH$_2$); 1.26 (3H, s, CH$_3$). MS m/z: 91, 216, 243, 303, 320 (100%, M).

(7a) (ST 1491)

Yield: 43%. M.p.: 238° C. MS (m/z): 230 (BP, M). $^1$H-NMR (200 MHz, CDCl$_3$): δ 8.00 (s, 2H triazole); 5.63 (br, 2H, NH$_2$); 4.06 (3H, s, N—CH$_3$); 2.64 (3H, s, C—CH$_3$).

(7e) (ST 2097)

6-amino-9-methyl-2-pentyl-8-(triazol-2-yl)-9(H)-purine

M.p.: 154° C. MS: m/z=286, 271, 257, 243, 230, 190 $^1$H-NMR (200 MHz, CDCl$_3$) δ (ppm): 8.00 (s, 2H), 7.26 (m, 10H), 5.56 (bs, 2H), 4.06 (s, 3H), 2.83 (t, 2H), 1.84 (m, 2H), 1.40 (m, 4H), 0.91 (m, 3H).

EXAMPLE 2

Scheme 2

4-hydroxy-3-nitropyridine (8)

16.7 ml of oleum (SO$_3$ 20% in H$_2$SO$_4$) was added slowly and dropwise to 20 ml of fuming nitric acid chilled to 0° C., and over a period of 15 minutes, 7 g of 4-hydroxypyridine were added. This was heated slowly until nitration began (red vapours developed). The reaction was then cooled until said vapours disappeared, then refluxed for 1 hour.

The reaction mixture was slowly cooled to room temperature and then poured over 50 g of ice. 60 ml of concentrated aqueous ammonia (30%) was added in small doses, taking care the temperature did not rise above 20° C. The pH was adjusted to 7.5 with more ammonia and then left at 4° C. overnight. The precipitate produced was filtered and crystallised in water to obtain 7.1 g of (8) as clear yellow crystals.

Yield=70%. M.p.: 275–277° C. MS (m/z): 94, 140.

4-chloro-3-nitropyridine (9)

In a reaction flask under nitrogen, were reacted at 70° C., 51.5 g of PCl$_5$ and 75 ml of POCl$_3$. At the same temperature was added carefully 34.6 g of (8). The temperature was increased to 140° C. and the reaction refluxed for 4 hours under nitrogen. To the cooled mixture, evaporated under vacuum, was added 100 ml of iced water. The pH was adjusted to 7.5 by the addition of granular sodium carbonate, and 60 ml of methylene chloride added and the mixture stirred vigorously until all the residue had completely dissolved. The phases were separated and the aqueous part was extracted with more methylene chloride (5×30 ml). The combined organic phases were treated with anhydrous sodium sulphate and evaporated to obtain 29.9 g of (9) as a yellow, waxy solid.

Yield=76%. MS (m/z): 85, 87, 100, 102, 112, 114, 158, 160 (M).

4-methylamino-3-nitropyridine (10)

29.9 g of (9) were solubilised in 200 ml of hot ethanol; to the solution, brought to 0° C., were added slowly, dropwise, 103 ml of 35% aqueous methylamine. This was left stirring for 30 minutes and then the ethanol evaporated. The residue was crystallised in water giving 24 g of (10) in the form of clear yellow crystals.

Yield=83%. MS (m/z): 107, 120, 135, 153 (M).

2-chloro-4-methylamino-3-aminopyridine (11)

10 g of (10) were dissolved in 50 ml of 12N HCl and the temperature brought to 90° C. 72.5 g di SnCl$_2$.2H$_2$O were added in five portions over the course of 1 minute. This was left stirring at 90° C. for 1 hour. After cooling the solution to room temperature, 100 ml of water were added and evaporated at reduced pressure. The residue was taken up in 100 ml of water, cooled to 0° C. and concentrated aqueous ammonia added, until the formation of a white, gelatinous precipitate. The pH was adjusted to 8.5–9 and the resulting emulsion centrifuged. The remaining solid residues were again taken up in water and centrifuged. The operation was repeated three times. The combined solid residues were left under stirring overnight in 50 ml of methylene chloride. The centrifuged aqueous phases were extracted three times with methylene chloride, then all the organic phases combined, then dried over anhydrous sodium sulphate and subsequently evaporated under vacuum, giving 6.2 g of (11) in the form of pink crystals.

Yield=60%. M.p.: 166–168° C. MS (m/z): 76, 122, 142, 157(M+).

4-chloro-1-methyl-1(H)-imidazo[4.5-c]pyridine (12)

2,4 g of (11) were suspended in 97 ml of ethyl orthoformate, and DMF added with agitation until the turbidity disappears. To the clear solution obtained was then added 1.7 ml of 12N HCl. (after a few minutes of the addition of the acid, the solution becomes turbid) and left under stirring, under nitrogen for 12 hours. The solvent was then evaporated under vacuum and the brown oily residue purified by flash chromatography (eluent: cyclohexane/ethyl acetate 20:80) giving 1.7 g of (17) as a white solid.

M.p.: 137–38° C. Yield=68%. MS: m/z: 167–169 (100%–30%: M+); 132 (55%: M+—Cl); 105 (35%). $^1$H-NMR (200 MHz, CDCl$_3$): δ 3.91 (s, 3H, N—CH$_3$); 7.33 (d, J=5.64 Hz, 1H, =N—CH=CH—), 7.98 (s, 1H, —N=CH—N(CH$_3$)—), 8.24 (d, J=5.64 Hz, 1H, =N—CH=CH—).

2-bromo-4-chloro-1-methyl-1 (H)-imidazo[4.5-c] pridine (13)

1.5 g (9 mmol) of (12) were solubilised, under nitrogen, in 25 ml of anhydrous THF and the temperature of the mixture adjusted to −78° C. 8 ml of BuLi 2.5 M (20 mmol) in hexane was added slowly. The solution took on a reddish colour in testimony to the formation of an aromatic carbanion in position 2. After 1 hour, 2 ml of bromine (40 mmol) were carefully added dropwise, over a period of 30 minutes and then left with agitation for a further 2 hours. The temperature was brought slowly to 0° C. and then a saturated solution of sodium metabisulphite added dropwise until the bromine was completely destroyed. The pH of the solution was adjusted to 9 with aqueous 2N sodium bicarbonate. The solution was extracted with methylene chloride. The combined organic phases were washed with salt water, dried over anhydrous sodium sulphate and evaporated under vacuum. A brownish solid was obtained which crystallised in water giving 1.4 g of (13) in the form of white crystals.

Yield=64%. MS: m/z: 245–247–249 (80%–100%–25%: M+); 210–212 (80%-75%: M+—Cl); 131 (100%: M+—Cl—Br), 105 (50%). $^1$H-NMR (200 MHz, CDCl$_3$): δ 3.84 (s, 3H, N—CH$_3$); 7.25 (d, J=6.11 Hz, 1H, =N—CH=CH—), 8.23 (d, J=6.11 Hz, 1H, =N—CH=CH—).

4-chloro-1-methyl-2-(triazol-2-yl)-1(H)-imidazo[4,5-c]pyridine (14) and 4-chloro-1-methyl-2-(triazol-1-yl)-1(H)-imidazo[4,5-c]pyridine (14a)

250 mg of NaH (80% in paraffin, 8.6 mmol) were suspended in 5 ml of anhydrous DMF and 0.5 ml (8.6 mmol) of 1(H)-1,2,3-triazole added. This was left under stirring at room temperature for one hour, then the temperature adjusted to 100° C. To this hot solution was added dropwise, over the course of 30 minutes, 1.4 g (5.7 mmol) of (13) emulsified in 15 ml of hot, anhydrous DMF. This was left under stirring at 100° C. for 4 hours, and then the temperature reduced to 60° C., and left to react overnight.

Upon termination of the reaction the DMF was evaporated and the solid residue crystallised in water.

The crystals were collected by filtration and the mother liquor extracted with methylene chloride, the organic phases combined and dried over sodium sulphate, evaporated and re-crystallised again in water. 614 mg of a mixture of (14 and 14a) were obtained, in the form of white crystals.

Total yield=46% (14+14a).

(14):

MS (m/z): 234–236 (100%–30%: M+); 207–209 (20%–5%: M+—HCN); 153–155 (40%–10%). $^1$H-NMR (CDCl$_3$, 200 MHz): δ 4.13 (s, 3H, N—CH$_3$); 7.35 (d, J=5.62 Hz, 1H, =N—CH=CH—), 8.05 (s, 2H, Triazole), 8.33 (d, J=5.62 Hz, 1H, =N—CH=CH—).

(14a):

MS (m/z): 234–236 (10%–3%: M+); 206–208 (100%–35%: M+—N$_2$); 191–193 (40%–15%). $^1$H-NMR (CDCl$_3$, 200 MHz): δ 4.23 (s, 3H, N—CH$_3$); 7.39 (d, J=5.80 Hz, 1H, =N—CH=CH—), 7.93 (d, J=1.19 Hz, 1H, Triazole), 8.34 (d, J=5.80 Hz, 1H, =N—CH=CH—), 8.65 (d, J=1.19 Hz, 1H, Triazole).

4-benzylamino-1-methyl-2-(triazol-2-yl)-1(H)-imidazo[4,5-c]pyridine (15)

In a flat-bottomed, long-necked reaction flask was suspended 1.4 g (5.5 mmol) of mixture (14, 14a), in 5 ml of benzylamine. The reaction was placed inside a microwave oven (frequency of irradiation: 2,450 MHz) and irradiated at 460 Watts until the benzylamine boiled. This was boiled for a few seconds and then the irradiation stopped and the mixture allowed to cool. This operation was repeated until the starting products had disappeared, as monitored by TLC. Following cooling, a yellow waxy mass was obtained which was further purified by flash chromatography (gradient: cyclohexane/ethyl acetate 4:6 (100 ml), cyclohexane/ ethyl acetate 2:8 (100 ml), ethyl acetate). 390 mg of (15) was obtained as a yellow solid.

Yield=29%. M.p.=180–184° C. MS (m/z): 305 (BP, M+); 250; 200, 174, 148. $^1$H-NMR (CDCl$_3$, 200 MHz): δ 4.02 (s, 3H, N—CH$_3$); 5.87 (bs, 2H), 7.29 (d, J=6.90 Hz, 1H), 7.40–7.50 (m, 5H) 7.88 (d, J=6.90 Hz, 1H), 8.29 (s, 2H, Triazole).

4-amino-1-methyl-2-(triazol-2-yl)-1(H)-imidazo[4,5-c]pyridino triflate (16) (ST 1680)

183 mg of (15) (0.6 mmol) were dissolved in 5 ml of anhydrous methylene chloride and 0.7 ml of trifluoromethanesulphonic acid (6 mmol) added slowly, dropwise. This was left to reflux for 1.5 hours. The reaction mixture was then chromatographed on an alumina column, eluted first with methylene chloride (100 ml), then with methylene chloride/ethanol 50/50 (100 ml) and finally with pure ethanol. The desired products were recovered in the alcoholic moieties. Following evaporation of the solvent, the residue was triturated using ethyl ether and then crystallised in ethanol. 52 mg of pure ST 1680, were obtained.

Yield=24%. M.p.: >290 (dec.)° C. MS (of the free base): m/z: 215 (100%: M+); 160 (40%–5%); 134 (35%). $^1$H-NMR (DMSO-d6, 200 MHz): δ 3.99 (s, 3H, N—CH$_3$); 7.37 (d, J=6.84 Hz, 1H, =NH+—CH=CH—), 7.82 (d, J=6.84 Hz, 1H, =NH+—CH=CH—), 8.41 (s, 2H, Triazole), 8.62 (br, 1H, NH$_2$), 12.94 (s, 2H, =NH+CH=CH—).

The compounds according to the present invention are ligands of the adenosine A$_{2a}$ receptor, in particular, they are selective antagonists, and as such are useful as medicaments, in particular for the treatment of pathologies benefiting from an antagonistic activity towards the A$_{2a}$ receptor.

Amongst the pathologies treated with the compounds of the present invention are motor disorders. As pathologies treated by the present invention we cite Alzheimer's disease, Huntington's disease, Wilson's disease and Parkinson's disease.

The present invention is also applied to Parkinson's disease associated with "on-off" phenomena, with preponderant dyskinesia.

In a preferred embodiment of the present invention, the compounds described are in combination with L-DOPA or with one or more dopamine agonists. In this case, the present invention is useful in dopamine substitutive therapy.

In another embodiment of the present invention, the compounds described above are useful as active ingredients for the preparation of a medicament for the treatment of cerebral ischaemia and-or the mechanisms associated with neurodegenerative processes.

Molecular Pharmacology

Affinity Towards the Adenosine A$_{2a}$ Receptor

The interactive capacity of each product towards the adenosine A$_{2a}$ receptor was evaluated using membranes from HEK 293 cells (human embryo kidney cells) stably expressing the human A$_{2a}$ receptor subtype exclusively.

The membranes were incubated with [3H]-CGS21680 at a concentration of 30 nM in a buffer comprised of 50 mM Tris (pH 7.4); 120 mM NaCl; 10 mM MgCl$_2$ mM CaCl$_2$, 2 U/ml of adenosine deaminase for 90' at 25° C. Non-specific binding was measured in the presence of NECA (50 μM).

Affinity Towards the Adenosine A$_{2b}$ Receptor

The interactive capacity of each product towards the adenosine A$_{2b}$ receptor was evaluated using membranes from HEK 293 cells stably expressing the human A$_{2b}$ receptor subtype exclusively.

These membranes were incubated with [$^3$H]-DPCPX at a concentration of 100 nM in a buffer comprised of 50 mM Tris (pH 7.4); 120 mM NaCl; 5 mM KCl; 10 mM MgCl$_2$; 2 mM CaCl$_2$, 2 U/ml of adenosine deaminase for 90' at 25° C. Non-specific binding was measured in the presence of NECA (50 μM).

Affinity Towards the Adenosine A$_1$ Receeotor

The interactive capacity of each product towards the adenosine A$_1$ receptor was evaluated using membranes from CHO-K1 cells which stably express the human A$_1$ subtype.

These membranes were incubated with [3H]-DPCPX at a concentration of 1.66 nM in a buffer comprised of 50 mM Tris (pH 7.4); 120 mM NaCl; 5 mM KCl; 10 mM MgCl$_2$; 2 mM CaCl$_2$, 2 U/ml of adenosine deaminase for 90' at 25° C. Non-specific binding was determined in the presence of DPCPX (8-Cyclopentyl-1,3-dipropylxanthine) at a concentration of 1 μM.

Affinity Towards the Adenosine A$_3$ Receptor

For compounds ST 1535 and ST 2097 their affinities towards the adenosine A$_3$ receptor were determined.

For this study, membranes from HEK-293 cells, which stably express the human A$_3$ subtype, were used, according to the method described by Salvatore et al. *Proc. Natl. Acad. Sci. USA*, 1999 90:10365–10369. The experimental conditions required the use of [$^{125}$I]AB-MECA as a radioligand at a concentration of 0.1 nM, an incubation time of 90 minutes at a temperature of 22° C., and IB-MECA (1 μM) for the determination of non-specific binding.

Analysis and Expression of the in Vitro Results

In binding studies for each compound, eight different concentrations (from $10^{-5}$ M to $10^{-12}$ M) were evaluated in order to obtain competition curves. By means of non-linear regression analysis of the competition curves, the IC$_{50}$ values, which express the binding affinity of each product, were determined. Using the Cheng Prusoff equation ($K_i=IC_{50}/1+(L/K_d)$) $K_i$ values were calculated through which the affinity of each product studied, for the receptor investigated, is expressed.

General Pharmacology

Evaluation of the Effects on Spontaneous Motor Activity in Mice

For this study, type CD1 male mice (n=8) were used. The effects of the products under study and of the reference compounds were evaluated using an apparatus consisting of a Plexiglas cage (40 cm×40 cm) surrounded by a series of photocells which monitor the movements of the animals placed inside, connected a computerised system, through which, the signals are collected and later elaborated.

Tests were carried out, after endoperitoneal administration of the products. 15 minutes after treatment, the treated animals, alternating with the controls, were placed inside the cage so as to record their spontaneous movements over a total period of 45 minutes broken down into two observation intervals (15'–45' and 45'–60', with respect to the time after treatment).

To examine the possible effects of the compounds studied on motor activity, the following parameters were considered: horizontal activity, vertical activity: total distance.

Except for CGS 21680 (reference compound, described in EP 0 277 917, Ciba-Geigy) which was dissolved in 0.9% NaCl, the products studied were solubilised in DMSO and then diluted in Cremofor EL and 0.9% NaCl (final concentrations: DMSO 15%, Cremofor EL 15%, NaCl 0.9%).

Evaluation of the Capacity of the Products to Induce Catalepsy in Mice.

10 CD1 male mice were used per group. For this test, a steel bar, 10 cm long, was placed at a height of 4.5 cm above the support surface. Onto this, were placed the front legs of the animals. The presence of catalepsy was determined by measuring the time (in seconds) the animal remained in the posture placed. Later, this parameter was placed relatively, on a scale of rising values (0 to 5) through which, the degree of catalepsy determined in both control animals and in these subjected to treatment with the substances under test could be proportionately expressed.

The reference products and these in this study were administered endoperitoneally, in a volume of 10 ml/kg, 30 minutes prior to the test.

Except for CGS 21680 (reference compound) which was dissolved in 0.9% NaCl, the products in the study and the control antagonist ZM 241385 were solubilised in DMSO and then diluted in Cremofor EL and 0.9% NaCl (final concentrations: DMSO 15%, Cremofor EL 15%, NaCl 0.9%).

Evaluation of the Capacity of the Products to Antagonise CGS 21680 Induced Catalepsy For this study, the product ST 1535 was used. Catalepsy was induced in the animals through the intracerebroventricular administration of CGS 21680 (10 µg/5 µl/mouse), 30 minutes prior to testing for the catalepsy score. The test compound was administered orally at a dose of 5 mg/Kg and 10 mg/Kg, 30 minutes prior to treatment with CGS 21680.

The catalepsy score was derived in the manner described following treatment with OGS 21680 after the following times: 30', 60'120', 180'.

Evaluation of the Capacity of the Products to Antagonise Haloperidol-Induced Catalepsy For this study, product ST 1535 was used. Catalepsy was induced in the animals through the endoperitoneal administration of Haloperidol at a dose of 4 mg/Kg, two hours prior measuring catalepsy in the animals, the presence of which was determined according to the method described previously.

After scoring for catalepsy by Haloperidol, the animals were treated orally, with a dose equal to 10 mg/kg and 20 mg/kg of the product ST 1535. Then 60 minutes after treatment, the animals were subjected to further catalepsy scoring, which was carried out at the following times after ST 1535 administration: 120', 240', 300'.

Effect of the Administration of Associated L-DOPA and $A_{2a}$ Antagonists on Haloperidol-induced Catalepsy.

For this study, product ST 1535 was used.

CD1 mice, divided into different experimental groups (n=10 per group) were used. All animals were subjected to treatment with Haloperidol (4 mg/kg, i.p.) two hours and 30' prior to the catalepsy test, carried out according to the method described above.

Later, the animals were subjected to different types of treatment according to their original experimental group (see diagram). All catalepsy evaluations were carried out 2 hours and 30 minutes after Haloperidol treatment.

Haloperidol+ST 1535: ST 1535 2.5 mg/kg, per os, 75' prior to testing;

Haloperidol+benserazide+L-Dopa: Benserazide 3.12 mg/kg i.p., 90' prior to testing;

L-DOPA: 12.5 mg/kg, 60' prior to testing;

Aloperidol+benserazide+L-Dopa+ST 1535: Benserazide 3.12 mg/kg i.p., 90' prior to testing;

ST 1535 1.25 mg/kg or 2.5 mg/kg, 75' prior to testing;

L-DOPA 12.5 mg/kg, 60' prior to testing;

$A_{2a}$ Antagonists and Antidepressant Activity. Forced Swim Test in Mice

Mice were dropped individually into glass cylinders (height: 25 cm, internal diameter.10 cm) containing 10 cm water, maintained at 23° C. The immobility time (sec) was measured during 4 minutes of test. A mouse was judged to be immobile when it remained floating in the water, making only the necessary movements to keep its head above water. Test compound ST 1535 was administered orally to mice, 60 minutes before the test.

In Vitro Activity

Table 1 reports values of the mean and standard deviations of the affinity towards the adenosine $A_{2a}$ receptor, expressed as $K_i$ (nM) for the various compounds studied.

It is possible to observe that the products denominated respectively ST 1535, ST 1537 and ST 2097 exhibit elevated interactive capacity towards the adenosine $A_{2a}$ receptor.

The comparison of the affinity values of these compounds, with these relative to the other products with adeninic structures, denotes that the substitution of adenine in position two, with relatively long alkyl chains (see ST 1535, ST 2097) or with significant steric hindrance (see ST 1537), favours an increase in affinity towards the $A_{2a}$ receptor.

In the same table are reported affinity values towards the adenosine receptor subtypes $A_{2b}$ and $A_1$, of each compound studied and, the ratio of receptor affinity ($K_iA_1/K_iA_{2a}$), through which is determined the selectivity of each product.

It is observed that compounds ST 1535, ST 1537 and ST 2097 possess an interactive capacity for the $A_{2a}$ receptor prevalent with respect to that demonstrated towards the $A_1$ and $A_{2b}$ subtypes, therefore, the compounds according to the present invention possess selective affinity towards the $A_{2a}$ receptor.

Furthermore, for compounds ST 1535 and ST 2097 the affinity for the adenosine $A_3$ receptor and for 36 receptors belonging to other neurotransmitters have been evaluated. In these binding studies, compounds of interest were initially tested at a concentration of 1 µM. Later, if the compound displaced more than 50% of the specific radioligand it was evaluated at 8 different product concentrations to determine the $IC_{50}$ values.

The results relating to this binding study are reported in table 2.

Compounds ST 1535 and ST 2097 display relatively low and negligible affinity towards the adenosine $A_3$ subtype and have no interactive capacity towards the other receptors ($IC_{50}$>1000 nM).

These results demonstrate that the compounds in the present invention are selective, having selective affinity for the adenosine $A_{2a}$ receptor.

TABLE 1

| Compound | $A_{2a}$ $K_i$ (nM) ± sd | $A_{2b}$ $K_i$ (nM) ± sd | $A_1$ $K_i$ (nM) ± sd | $K_iA_1/K_iA_{2a}$ |
| --- | --- | --- | --- | --- |
| ST 1680 | 97 ± 23 | 926 ± 55 | 1563 ± 252 | 16 |
| ST 1491 | 70 ± 15 | | 10 ± 1.4 | 0.15 |
| ST 1535 | 2.29 ± 0.58 | 627 ± 45 | 107 ± 40 | 47 |
| ST 2097 | 0.12 ± 0.033 | 153 ± 13 | 26.2 ± 6.55 | 217 |
| ST 1537 | 2.34 ± 0.69 | 2330 ± 588 | 80 ± 13 | 34 |
| ST 1490 | 46 | | 0.43 | 0.009 |
| CGS 21680 | 51 ± 13 | | | |
| ZM 241385 | 0.11 ± 0.03 | | | |
| Alloxazine | | 3.8 ± 2.1 | | |
| DPCPX | | | 6.5 ± 0.95 | |

TABLE 2

| Receptors | ST 1535 1 μM Ki (nM) | ST 2097 1 μM Ki (nM) | Reference compounds | IC$_{50}$ (nM) | Ki (nM) |
|---|---|---|---|---|---|
| A$_3$ (h) | | 1580 | | 519 | IB-MECA | 1.2 | 0.84 |
| ADO$_{transporter}$ | 24 | 34 | NBTI | 0.30 | |
| α$_1$(non-selective) | — | — | prazosin | 0.86 | |
| α$_2$(non-selective) | — | — | yohimbine | 95 | |
| β$_1$ | — | — | atenolol | 1,770 | |
| β$_2$ | — | — | ICI 118551 | 2.3 | |
| BZD (central) | — | — | diazepam | 12 | |
| D1 | — | — | SCH 23390 | 0.66 | |
| D2 | — | — | (+)butaclamol | 8.9 | |
| D3 | — | — | (+)butaclamol | 5.1 | |
| D4.4 (h) | — | — | clozapine | 156 | |
| D5 (h) | — | — | SCH 23390 | 0.61 | |
| GABAa | — | — | muscimol | 16 | |
| GABAb | — | — | baclofen | 50 | |
| GABA$_{transporter}$ | — | — | Nipecotic acid | 10,100 | |
| AMPA | — | — | L-glutamate | 613 | |
| Kainate | — | — | Kainic acid | 77 | |
| PCP | — | — | MK-801 | 2.0 | |
| P2X | — | — | α,β-MeATP | 14 | |
| P2Y | — | — | dATPα S | 22 | |
| NMDA | — | — | CGS 19755 | 967 | |
| H$_1$ (central) | — | — | pyrilamine | 1.3 | |
| M$_1$ | — | — | pirenzepina | 22 | |
| M$_2$ | — | — | methoctramine | 34 | |
| M$_3$ | — | — | 4-DAMP | 3.5 | |
| M$_4$ | — | — | 4-DAMP | 1.9 | |
| M$_5$ | — | — | 4-DAMP | 2.0 | |
| Choline$_{transporter}$ | — | — | Hemicholinium-3 | 12 | |
| Opiate (non-selective) | — | — | naloxone | 1.6 | |
| 5-HT$_{1A}$ | — | — | 8-OH-DPAT | 0.66 | |
| 5-HT$_{2A}$ | — | — | ketanserin | 2.7 | |
| 5-HT$_{2C}$ (h) | — | — | mesulergine | 1.9 | |
| 5-HT$_3$ (h) | — | — | MDL 72222 | 9.3 | |
| 5-HT$_4$ | — | — | | | |
| 5-HT$_{5A}$ (h) | — | — | serotonin | 79 | |
| 5-HT$_6$ (h) | — | — | serotonin | 421 | |
| NE transporter | — | — | protriptyline | 1.1 | |
| DA transporter | — | — | GBR 12909 | 5.0 | |
| 5-HT transporter | — | 13 | imipramine | 4.4 | |

For the test compounds, the results are expressed as a percent inhibition of control specific binding (mean values; n = 2).
The symbol — indicates an inhibition of less than 10%.

In Vivo Activity

To define the activity profile (agonistic or antagonistic) possessed by the compounds of interest, their effects on motor activity in mice were examined. These were compared to these brought about by the following reference compounds CGS 21680 (selective agonist of the A$_{2a}$ receptor, EP 0 277 917) and ZM 241385 (selective antagonist of the A$_{2a}$ receptor). It is noted that the agonists induce a depression in motor activity, whilst the antagonists have stimulatory effects (Nikodijevicc O., et. al. *J.Pharm. Exp. Ther* 257, 286–94, 1991).

In table 3, the results of the effects induced by compounds of interest and reference, on three parameters describing spontaneous motor activity in mice are illustrated The values of the mean and the standard error of each parameter observed are reported.

TABLE 3

| | Horizontal activity | | Vertical activity | | Total distance | |
|---|---|---|---|---|---|---|
| | Intervals of observation from the treatment | | | | | |
| Treatment | 15'–45 | 45'–60 | 15'–45 | 45'–60' | 15'–45' | 45'–60' |
| Controls | 5992 ± 484 | 3148 ± 1004 | 356 ± 62 | 117 ± 40 | 1394 ± 148 | 469 ± 125 |
| CGS 21680 (0.5 mg/kg) | 1608 ± 328 | 471 ± 254 | 27 ± 11 | 10 ± 1 | 504 ± 106 | 121 ± 73 |
| Vehicle (10 ml/kg) | 5890 ± 856 | 2259 ± 452 | 330 ± 96 | 119 ± 34 | 1315 ± 290 | 412 ± 121 |
| ZM 241385 (15 mg/kg) | 8706 ± 473 | 4148 ± 241 | 680 ± 64 | 362 ± 78 | 2280 ± 242 | 1022 ± 130 |

TABLE 3-continued

| Treatment | Horizontal activity | | Vertical activity | | Total distance | |
|---|---|---|---|---|---|---|
| | \multicolumn{6}{c}{Intervals of observation from the treatment} | | | | | |
| | 15'–45 | 45'–60 | 15'–45 | 45'–60' | 15'–45' | 45'–60' |
| ZM 241385 (30 mg/kg) | 7035 ± 709 | 3505 ± 375 | 613 ± 102 | 282 ± 37 | 1725 ± 186 | 783 ± 165 |
| ZM 241385 (60 mg/kg) | 7790 ± 980 | 4241 ± 407 | 570 ± 129 | 264 ± 56 | 2250 ± 401 | 1131 ± 158 |
| ST 1537 (2.5 mg/kg) | 7494 ± 565 | 3133 ± 250 | 590 ± 78 | 210 ± 17 | 1676 ± 204 | 677 ± 105 |
| ST 1537 (5 mg/kg) | 7203 ± 264 | 2844 ± 299 | 498 ± 77 | 363 ± 91 | 1503 ± 116 | 532 ± 95 |
| ST 1537 (10 mg/kg) | 8242 ± 847 | 3874 ± 295 | 528 ± 126 | 276 ± 57 | 2707 ± 950 | 843 ± 149 |
| Vehicle (10 ml/kg) | 5184 ± 832 | 1734 ± 367 | 123 ± 60 | 49 ± 25 | | |
| ST 1535 (2.5 mg/kg) | 5386 ± 505 | 1693 ± 266 | 282 ± 79 | 68 ± 21 | | |
| ST 1535 (5 mg/kg) | 7549 ± 508 | 2353 ± 199 | 249 ± 41 | 76 ± 16 | | |
| ST 1535 (10 mg/kg) | 7434 ± 526 | 2784 ± 345 | 219 ± 64 | 71 ± 32 | | |
| ST 1535 (20 mg/kg) | 10524 ± 670 | 3321 ± 363 | 486 ± 84 | 148 ± 36 | | |

Regarding compounds in the present invention, in particular product ST 1537 induces a clear increase in motor activity. In fact, independently of the product dosage administered, each of the parameters examined is significantly increased with respect to control values. Furthermore, it is observed that compound ST 1537 is more active than the reference antagonist. In fact, the minimum dose of ST 1537 induces the same effects as these produced, with a greater dose (15 mg/kg), of compound ZM 241385. Also for compound ST 1535 a significant increase of the spontaneous motor activity in mice is observed, starting from a dose of 5 mg/Kg. Therefore, the compounds in the present invention possess an antagonistic activity towards the adenosine $A_{2a}$ receptor.

Figure 1:
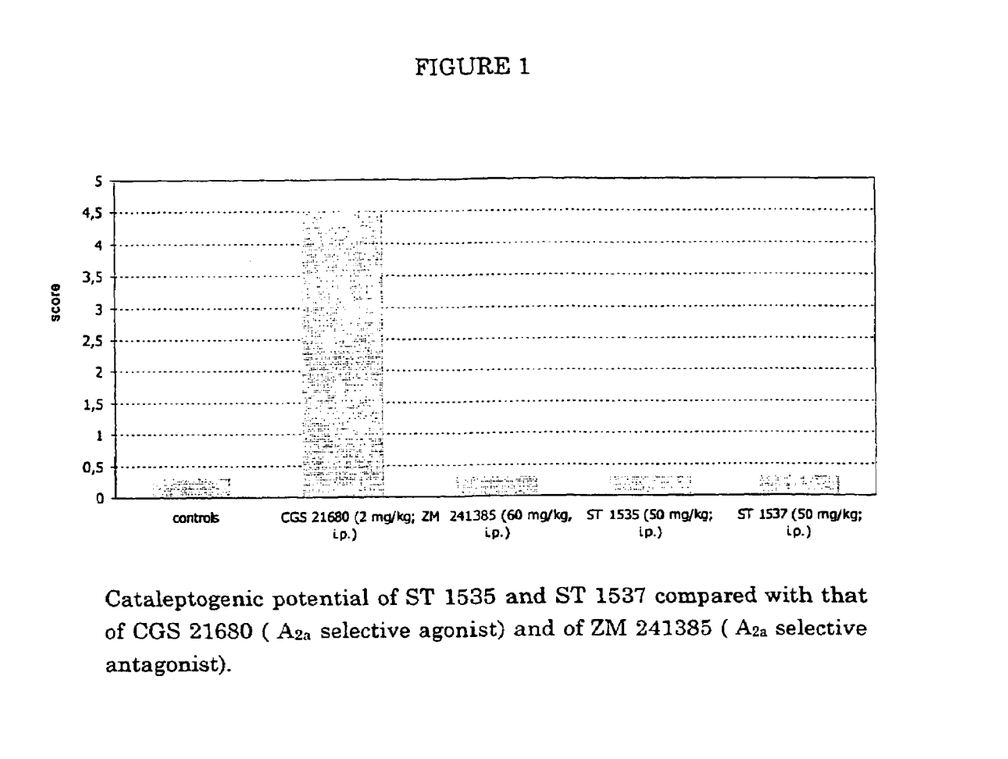
in FIG. 1 it is shown the evaluation of the capacity to induce catalepsy in mice.

Along with these observations, the evaluation of the eventual presence of catalepsy in the animals, following treatment with the products studied (FIG. 1), confirms an antagonistic profile for ST 1537 and for ST 1535. In fact, none of them brought about the appearance of catalepsy in mice, analogous to the reference antagonist (ZM 241385, 60 mg/kg) and in contrast to that demonstrated by the reference agonist (CGS 21680, 2 mg/kg).

Figure 2:
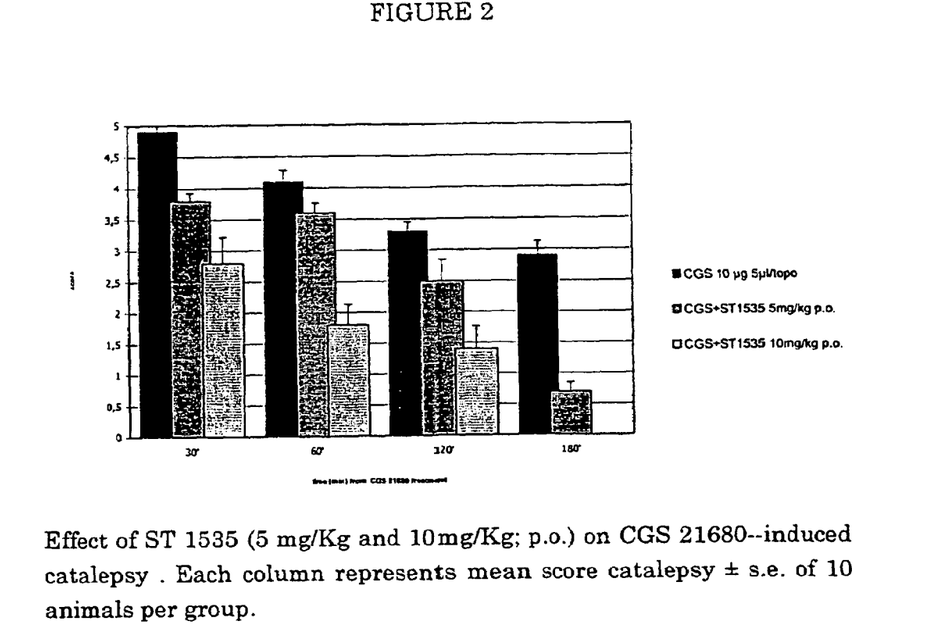
in FIG. 2 it is shown the effect of exemplary compounds of the present invention on CGS 21680—induced catalepsy. Each column represents mean score catalepsy±s.e. of 10 animals per group.

For compound ST 1535 the profile of antagonistic activity towards the $A_{2a}$ receptor has been demonstrated also through the evaluation of its capacity to antagonise the disappearance of catalepsy previously induced by the administration of the selective $A_{2a}$ receptor agonist: CGS21680 (FIG. 2).

The selective $A_{2a}$ receptor agonist induced an elevated degree of catalepsy in the animals. The product ST 1535, administered orally, significantly antagonises the appearance of catalepsy at all the observed times, particularly when the dose administered is 10 mg/kg. This result confirms and describes the antagonistic activity profile towards the adenosine $A_{2a}$ receptor of preferred compound ST 1535.

Figure 3:
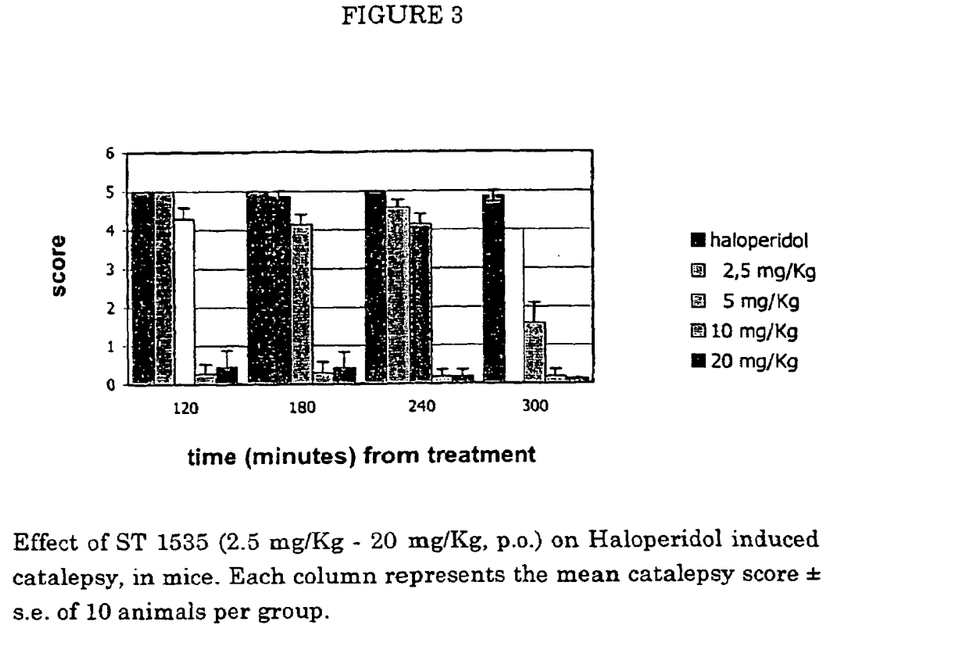
in FIG. 3 it is shown the effect of exemplary compounds of the present invention on Haloperidol-induced catalepsy, in mice. Each column represents the mean catalepsy score±s.e. of 10 animals per group.

The profile as selective antagonist for the adenosine $A_{2a}$ receptor of ST 1535 was confirmed also through the study of the effects of the compound on Haloperidol catalepsy in mice. Furthermore, through this evaluation the products capacity to modulate a dysfunction of dopaminergic transmission in the nigrostriatal system was determined. In FIG. 3 it is observed that after oral administration, ST 1535 reduces the appearance of catalepsy in mice, a behavioural manifestation promoted by a reduction of the dopaminergic tone in the nigrostriatal system, following acute administration of Haloperidol. The anticataleptic activity of ST 1535 demonstrates, indirectly, that the compound of interest is capable of compensating the deficiency in dopaminergic neurotransmission brought about in the nigrostriatal system following treatment with Haloperidol, according to the pharmacological characteristics belonging to selective antagonists of the adenosine $A_{2a}$ receptor.

Figure 4:
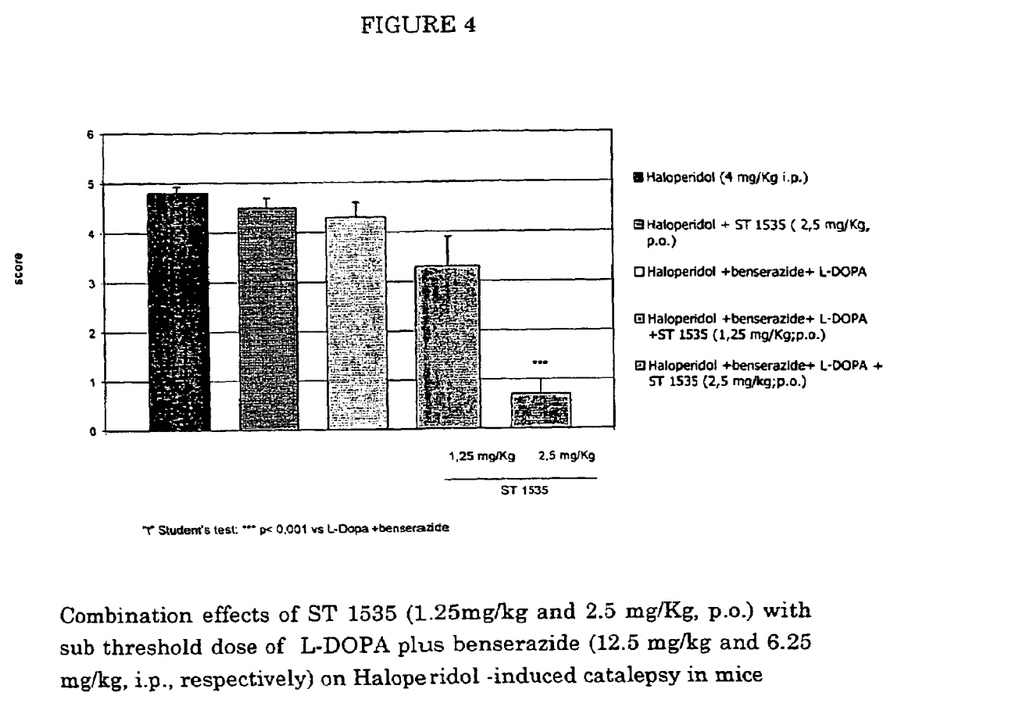
in FIG. 4 it is shown the combination effects of exemplary compounds of the present invention with sub threshold dose of L-DOPA plus benserazide (12.5 mg/kg and 6.25 mg/kg, i.p., respectively) on Haloperidol-induced catalepsy in mice.

Furthermore, for the preferred compound ST 1535 it has been demonstrated that the oral administration of the product potentiates the anticataleptic activity of treatment with ineffective doses of L-DOPA and benserazide. The results of this evaluation are reported in FIG. 4. Treatment with ST 1535 associated with ineffective doses of L-DOPA and benserazide reduce Haloperidol-Catalepsy, in a Dose-Dependent Manner.

These results suggest that the product of interest ST 1535 can be administered in combination with low doses of L-DOPA for the treatment of Parkinson's disease.

L-DOPA is commonly used for the treatment of Parkinson's disease. Yet, the use of L-DOPA becomes limited due to the appearance of dyskinesia as a side effect (Shaw K. M. et al. "Q.J.Med" 1980 49, 283). The co-administration of ST 1535 could reduce the quantity of L-DOPA to be administered, reducing the appearance of said side effects.

Figure 5:
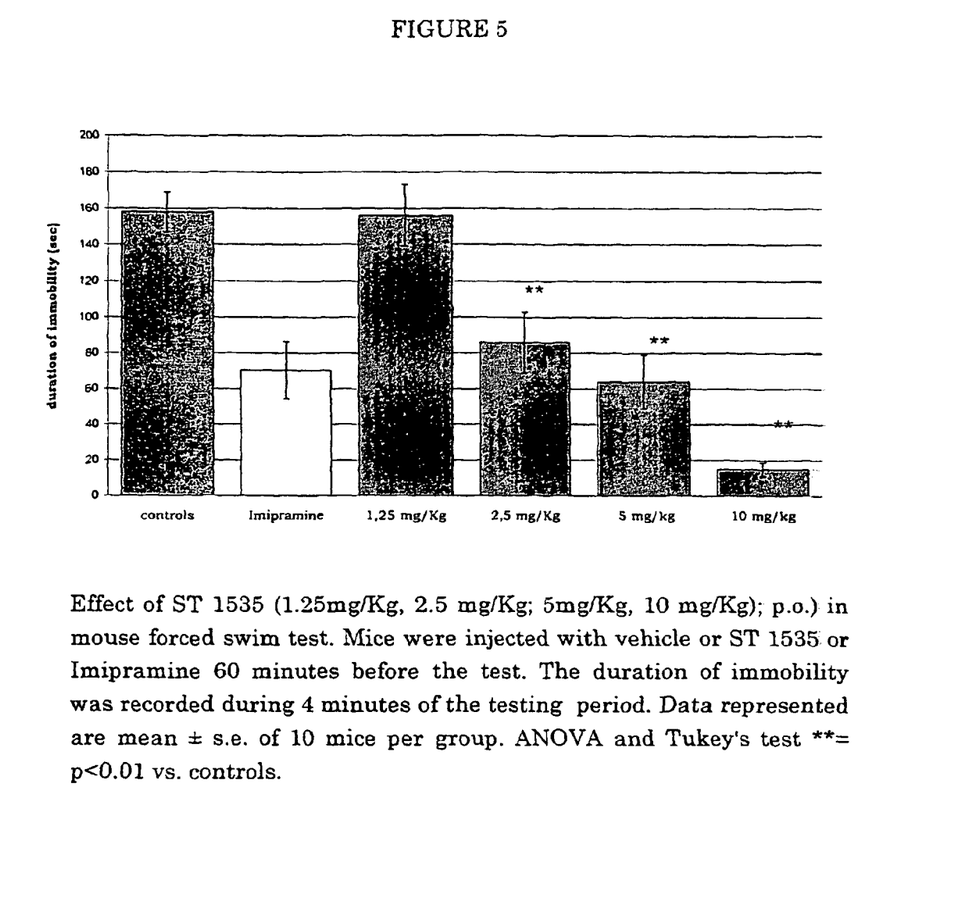
in FIG. 5 it is shown the effect of exemplary compounds of the present invention in mouse forced swim test. Mice were injected with vehicle or the test compound or Imipramine 60 minutes before the test.

Furthermore, for the preferred compound ST 1535 an antidepressant activity was measured. It is noted that selective antagonists of the $A_{2a}$ receptor are being defined as new potential antidepressants (El Yacobui M. et al. British J. Pharmacol. 2001:134,68–77). FIG. 5 represents the effects of ST 1535 in an animal model for depression. The compound reduces, in a dose-dependant manner, the time of immobility of the animal, in a manner similar to that observed for the antidepressive drug Imipramine.

A further object of the present invention are pharmaceutical compositions comprising, as active ingredient, at least one formula (I) compound, alone or in combination with one or more other formula (I) compounds, or, said formula (I) compound or compounds in combination with other active ingredients useful in the treatment of the pathologies indicated here, for example other products with activity towards the adenosine $A_{2a}$ receptor; even in separate dosage forms or in forms adapted to combined therapies. The active ingredients in the present invention will be in mixtures with appropriate vehicles and/or excipients commonly used in pharmaceutical techniques, as for example, described in "Remington's Pharmaceutical Sciences Handbook", latest edition. The compositions according to the present invention will contain a therapeutically effective amount of the active ingredient. The dosages will be determined by a person skilled in the art, for example clinicians and doctors, according to the type of pathology to be treated and the conditions of the patients, or in concurrence with the administration of other active ingredients.

Examples of pharmaceutical compositions are those that permit oral or parenteral, intravenous, intramuscular, subcutaneous, transdermal administration. Pharmaceutical compositions suitable to this purpose are: pills, rigid or soft capsules, powders, solutions, suspensions, syrups, solid forms for extemporary liquid composition. Compositions for parenteral administration are for example all the forms injectable intramuscularly, endovenously, subcutaneously, in the form of solutions, suspensions, emulsions. We also mention liposomal formulations. Also included are the controlled-release forms of the active ingredient, both for oral administration, pills covered with appropriate layers, microencapsulated powders, complexes with cyclodextrine, depot forms, for example subcutaneous, such as injectable deposits or implants.

The invention claimed is:

1. A compound of the formula (I)

wherein: X is N;
R1 is $C_1$–$C_6$ linear or branched alkyl or $C_2$–$C_6$ linear or branched alkenyl;

R2 is hydrogen, $C_1$–$C_6$ linear or branched alkyl or $C_2$–$C_6$ linear or branched alkenyl $C_6$–$C_{14}$ aryl or $C_6$–$C_{14}$ aryl($C_1$–$C_6$) linear or branched alkyl or $C_6$–$C_{14}$ aryl ($C_2$–$C_6$) linear or branched alkenyl, with the aryl group optionally substituted by one or more substituents, either the same or different, selected from the group consisting of halogen, hydroxy, $C_1$–$C_6$ alkoxy linear or branched or $C_2$–$C_6$ alkenyloxy linear or branched, amino, optionally mono- or disubstituted with $C_1$–$C_6$ linear or branched alkyl;

R3 is $NH_2$, $NHR_4$ $R_4$ is $C_1$–$C_6$ alkyl or $C_1$–$C_6$ hydroxyalkyl, $C_1$–$C_3$ alkoxyalkyl, amino($C_1$–$C_6$)alkyl, where the amino group is optionally substituted with one or two $C_1$–$C_3$ linear or branched alkyl groups, or with one or two $C_2$–$C_3$ alkenyl groups $C_6$–$C_{14}$ aryl or $C_6$–$C_{14}$ aryl($C_1$–$C_6$) alkyl, with the aryl group optionally substituted by one or more substituents, either the same or different, selected from the group consisting by halogen, hydroxy, $C_1$–$C_6$ alkoxy linear or branched or $C_2$–$C_6$ alkenyloxy linear or branched, amino, mono- or di-substituted with $C_1$–$C_6$ alkyl linear or branched or $C_2$–$C_6$ alkenyl linear or branched; and pharmaceutically acceptable salts thereof.

2. The compounds according to claim 1 wherein X is nitrogen and $R_2$ is n-butyl in position 2.

3. The compounds according to claim 1, wherein X is nitrogen and $R_2$ is phenethyl in position 2.

4. The compounds according to claim 1, wherein X is nitrogen and $R_2$ is n-pentyl in position 2.

5. The compounds according to claim 1, selected from the group consiting of:
   6-amino-2,9-dimethyl-8-(triazol-2-yl)-9(H)-purine;
   2-butyl-9-methyl-8-(2H-1,2,3-triazol-2-yl)-9H-purine-6-ylamine;
   9-methyl-2-(2-phenylethyl)-8-(2H-1,2,3-triazol-2-yl)-9H-purine-6-ylamine;
   9-methyl-2-pentyl-8-(2H-1,2,3-triazol-2-yl)-9H-purine-6-ylamine.

6. The compund according to claim 1, which is 6-amino-9-methyl-8-(2H-1,2,3,-triazol-2-yl)-9H-purine.

* * * * *

UNITED STATES PATENT AND TRADEMARK OFFICE
CERTIFICATE OF CORRECTION

PATENT NO.        : 7,230,102 B2                                                  Page 1 of 1
APPLICATION NO. : 10/484491
DATED             : June 12, 2007
INVENTOR(S)       : Tarzia It is certified that error appears in the above-identified patent and that said Letters Patent is hereby corrected as shown below:

Title Page - should read
(75) Inventors: Giorgio TARZIA, Rome (IT); Giovanni PIERSANTI, Rome (IT); Patrizia MINETTI, Rome (IT): Maria Assunta DI CESARE, Rome (IT); Grazia GALLO, Rome (IT); Fabrizio GIORGI, Rome (IT); Luca GIORGI, Rome (IT)

Col 26 lines 33-41
5. The compounds according to claim 1, selected from the group consisting of:

6-amino-2,9-dimethyl-8-(triazol-2-yl)-9(H)-purine;

9-methyl-2-(2-phenylethyl)-8-(2H-1,2,3-triazol-2-yl)-9H-purine-6-ylamine;

9-methyl-2-pentyl-8-(2H-1,2,3-triazol-2-yl)-9H-purine-6-ylamine.

Should read:

5. The compounds according to claim 1, selected from the group consisting of:

6-amino-2,9-dimethyl-8-(2H-1,2,3-triazol-2-yl)-9(H)-purine;

2-butyl-9-methyl-8-(2H-1,2,3-triazol-2-yl)9H-purine-6-ylamine;

9-methyl-2-(2-phenylethyl)-8-(2H-1,2,3-triazol-2-yl)-9H-purine-6-ylamine;

9-methyl-2-pentyl-8-(2H-1,2,3-triazol-2-yl)-9H-purine-6-ylamine.

Signed and Sealed this

Sixth Day of November, 2007

JON W. DUDAS
*Director of the United States Patent and Trademark Office*